United States Patent
Shapland et al.

(10) Patent No.: US 9,050,400 B2
(45) Date of Patent: Jun. 9, 2015

(54) REMOTE SENSING CATHETER SYSTEM AND METHODS

(75) Inventors: James Edward Shapland, St. Paul, MN (US); Tuan M. Doan, Burnsville, MN (US); Christopher G. Quinn, Minneapolis, MN (US)

(73) Assignee: Osprey Medical, Inc., Wilmington, DE (US)

( * ) Notice: Subject to any disclaimer, the term of this patent is extended or adjusted under 35 U.S.C. 154(b) by 0 days.

(21) Appl. No.: 12/228,534

(22) Filed: Aug. 12, 2008

(65) Prior Publication Data

US 2010/0042069 A1    Feb. 18, 2010

(51) Int. Cl.
*A61M 31/00*     (2006.01)
*A61M 1/00*      (2006.01)

(52) U.S. Cl.
CPC ....... *A61M 1/0031* (2013.01); *A61M 2202/049* (2013.01)

(58) Field of Classification Search
CPC .............. A61M 1/0031; A61M 2202/049
USPC ............... 604/27, 65, 510, 4.01; 600/433
See application file for complete search history.

(56) References Cited

U.S. PATENT DOCUMENTS

| | | | |
|---|---|---|---|
| 3,931,815 A | 1/1976 | Takatsuki | |
| 4,054,137 A | 10/1977 | Lee et al. | |
| 4,581,017 A | 4/1986 | Sahota | |
| 4,592,341 A | 6/1986 | Omagari et al. | |
| 4,795,427 A | 1/1989 | Helzel | |
| 4,838,872 A | 6/1989 | Sherlock | |
| 4,969,470 A | 11/1990 | Mohl et al. | |
| 5,069,662 A | 12/1991 | Bodden | |
| 5,338,662 A | 8/1994 | Sadri | |
| 5,423,745 A | 6/1995 | Todd et al. | |
| 5,494,822 A | 2/1996 | Sadri | |
| 5,807,311 A | 9/1998 | Palestrant | |
| 5,807,318 A | 9/1998 | St. Goar et al. | |
| 5,807,322 A | 9/1998 | Lindsey et al. | |
| 5,810,757 A | 9/1998 | Sweezer, Jr. et al. | |
| 5,813,842 A | 9/1998 | Tamari | |
| 5,871,464 A | 2/1999 | Tryggvason et al. | |
| 5,871,465 A | 2/1999 | Vasko | |
| 6,021,340 A | 2/2000 | Randolph et al. | |
| 6,080,170 A | 6/2000 | Nash et al. | |
| 6,093,392 A | 7/2000 | High et al. | |
| 6,110,139 A | 8/2000 | Loubser | |

(Continued)

FOREIGN PATENT DOCUMENTS

| DE | 10102045 | 1/2003 |
|---|---|---|
| EP | 0 301 854 | 2/1989 |

(Continued)

OTHER PUBLICATIONS

Texas heart Institute Journal; Transcatheter Coronary Artery Diagnostic Techniques, vol. 16, No. 3, dated: 1989; 9 pgs.

(Continued)

*Primary Examiner* — Kami A Bosworth
*Assistant Examiner* — Imani Hayman
(74) *Attorney, Agent, or Firm* — Merchant & Gould P.C.

(57) ABSTRACT

A remote sensing catheter system including an injection catheter and a collection catheter. In one method of use, an external sensor of the system determines the timing of operation of the collection catheter. In another method of use, a sensor determines the volume of medium in the injection.

8 Claims, 3 Drawing Sheets

(56) References Cited

U.S. PATENT DOCUMENTS

| | | | |
|---|---|---|---|
| 6,152,141 A | 11/2000 | Stevens et al. | |
| 6,186,146 B1 | 2/2001 | Glickman | |
| 6,251,093 B1 | 6/2001 | Valley et al. | |
| 6,254,563 B1 | 7/2001 | Macoviak et al. | |
| 6,295,990 B1 | 10/2001 | Lewis et al. | |
| 6,342,214 B1 | 1/2002 | Tryggvason et al. | |
| 6,376,471 B1 | 4/2002 | Lawrence, III et al. | |
| 6,398,752 B1 | 6/2002 | Sweezer et al. | |
| 6,481,439 B1 | 11/2002 | Lewis et al. | |
| 6,500,158 B1 | 12/2002 | Ikeguchi | |
| 6,508,777 B1 | 1/2003 | Macoviak et al. | |
| 6,554,819 B2 | 4/2003 | Reich | |
| 6,558,349 B1 | 5/2003 | Kirkman | |
| 6,569,147 B1 | 5/2003 | Evans et al. | |
| 6,585,716 B2 | 7/2003 | Altman | |
| 6,595,963 B1 | 7/2003 | Barbut | |
| 6,638,264 B1 | 10/2003 | Tryggvason et al. | |
| 6,638,268 B2 | 10/2003 | Niazi | |
| 6,673,039 B1 | 1/2004 | Bridges et al. | |
| 6,689,090 B1 | 2/2004 | Tryggvason et al. | |
| 6,699,231 B1 | 3/2004 | Sterman et al. | |
| 6,726,651 B1 | 4/2004 | Robinson et al. | |
| 6,935,344 B1 | 8/2005 | Aboul-Hosn et al. | |
| 6,980,843 B2 | 12/2005 | Eng et al. | |
| 6,992,070 B2 | 1/2006 | Donahue et al. | |
| 7,211,073 B2 | 5/2007 | Fitzgerald et al. | |
| 7,300,429 B2 | 11/2007 | Fitzgerald et al. | |
| 7,331,922 B2 | 2/2008 | Mohl | |
| 7,363,072 B2 | 4/2008 | Movahed | |
| 7,722,596 B2 | 5/2010 | Shapland et al. | |
| 8,152,786 B2 | 4/2012 | Shapland et al. | |
| 2001/0052345 A1 | 12/2001 | Niazi | |
| 2002/0062121 A1 | 5/2002 | Tryggvason et al. | |
| 2002/0077595 A1* | 6/2002 | Hundertmark et al. | .. 604/103.09 |
| 2002/0091349 A1 | 7/2002 | Reich | |
| 2002/0099254 A1 | 7/2002 | Movahed | |
| 2002/0107504 A1 | 8/2002 | Gordon | |
| 2002/0165598 A1 | 11/2002 | Wahr et al. | |
| 2002/0169436 A1 | 11/2002 | Gurm et al. | |
| 2003/0138350 A1 | 7/2003 | Macoviak | |
| 2003/0163081 A1 | 8/2003 | Constantz et al. | |
| 2003/0191434 A1 | 10/2003 | Dorros et al. | |
| 2003/0236533 A1 | 12/2003 | Wilson et al. | |
| 2004/0002159 A1 | 1/2004 | Xiao et al. | |
| 2004/0030286 A1 | 2/2004 | Altman | |
| 2004/0099596 A1 | 5/2004 | Naghavi et al. | |
| 2004/0102732 A1 | 5/2004 | Naghavi et al. | |
| 2004/0102766 A1 | 5/2004 | Poleo, Jr. | |
| 2004/0210239 A1 | 10/2004 | Nash et al. | |
| 2004/0254523 A1* | 12/2004 | Fitzgerald et al. | ............ 604/21 |
| 2005/0010189 A1 | 1/2005 | Toomey et al. | |
| 2005/0124969 A1 | 6/2005 | Fitzgerald et al. | |
| 2005/0192548 A1 | 9/2005 | Dolliver et al. | |
| 2005/0197531 A1 | 9/2005 | Cabiri et al. | |
| 2005/0226855 A1 | 10/2005 | Alt et al. | |
| 2005/0256441 A1 | 11/2005 | Lotan et al. | |
| 2005/0273014 A1 | 12/2005 | Gianchandani et al. | |
| 2006/0013772 A1 | 1/2006 | LeWinter et al. | |
| 2007/0078352 A1 | 4/2007 | Pijls | |
| 2007/0118072 A1 | 5/2007 | Nash | |
| 2007/0203445 A1 | 8/2007 | Kaye et al. | |
| 2007/0255162 A1 | 11/2007 | Abboud et al. | |
| 2008/0021314 A1 | 1/2008 | Movahed | |
| 2008/0108960 A1 | 5/2008 | Shapland et al. | |
| 2008/0125698 A1 | 5/2008 | Gerg et al. | |
| 2008/0125746 A1 | 5/2008 | Shapland et al. | |
| 2008/0306425 A1 | 12/2008 | Al-Rashdan | |
| 2009/0018526 A1 | 1/2009 | Power | |
| 2009/0069829 A1 | 3/2009 | Shturman | |
| 2009/0187131 A1* | 7/2009 | Fitzgerald et al. | ........... 604/6.09 |
| 2009/0234321 A1 | 9/2009 | Shapland et al. | |
| 2010/0041984 A1 | 2/2010 | Shapland et al. | |
| 2010/0082004 A1 | 4/2010 | Shapland et al. | |
| 2010/0168564 A1 | 7/2010 | Shapland et al. | |
| 2010/0274173 A1 | 10/2010 | Shapland et al. | |
| 2011/0015558 A1 | 1/2011 | Kaye et al. | |
| 2011/0172558 A1 | 7/2011 | Shapland et al. | |
| 2013/0079697 A1 | 3/2013 | Kaye | |

FOREIGN PATENT DOCUMENTS

| | | |
|---|---|---|
| EP | 0 150 960 | 1/1990 |
| EP | 0 526 102 | 4/1998 |
| EP | 1859826 | 11/2007 |
| GB | 2 125 487 A | 3/1984 |
| JP | 2001 526071 | 12/2001 |
| WO | WO 89/01309 | 2/1989 |
| WO | WO 92/20387 | 11/1992 |
| WO | WO 98/31405 | 7/1998 |
| WO | WO 98/56440 | 12/1998 |
| WO | WO 99/06097 | 2/1999 |
| WO | WO 99/29227 | 6/1999 |
| WO | WO 99/30765 | 6/1999 |
| WO | WO 99/31982 | 7/1999 |
| WO | WO 01/00268 | 1/2001 |
| WO | WO 01/13983 | 3/2001 |
| WO | WO 01/83004 | 11/2001 |
| WO | WO 01/97901 A2 | 12/2001 |
| WO | WO 02/060511 | 8/2002 |
| WO | WO 02/087677 | 11/2002 |
| WO | WO 03/070330 | 8/2003 |
| WO | WO 2004/083817 A2 * | 9/2004 |
| WO | WO 2005/027995 | 3/2005 |
| WO | WO 2005/082440 | 9/2005 |
| WO | WO 2006/004882 | 1/2006 |
| WO | WO 2006/004882 A1 | 1/2006 |
| WO | WO 2006/042219 | 4/2006 |
| WO | WO 2007/002154 | 1/2007 |
| WO | WO 2007/143288 | 12/2007 |
| WO | WO 2008/122048 | 10/2008 |

OTHER PUBLICATIONS

Alfayoumi, F. et al., The No-Reflow Phenomenon: Epidemiology, Pathophysiology and Therapeutic Approach, Review in Cardiovascular Medicine, vol. 6, No. 2, (2005); pp. 72-83.

Assali, A. et al., "Intracoronary Adenosine Administered During Precutaneous Intervention in Acute Myocardial Infarction and Reduction in the Incidence of "No Reflow" Phenomenon", Catheterization and Cardiovascular Interventions, vol. 51 (2000); pp. 27-31.

De Lentos, J. et al., "New Tools for Assessing Microvascular Obstructions in Patients with ST Elevation Myocardial Infarction", Heart, vol. 90, (2004); pp. 119-120.

Kramer, C., "The Prognostic Significance of Microvascular Obstruction After Myocardial Infarction as Defined by Cardiovascular Magnetic Resonance", European Heart Journal, vol. 26, (2005): pp. 532-533.

Marzilli, M et al., "Primary Coronary Angioplasty in Acute Myocardial Infarction: Clincial Correlates of he "No Reflow" Phenomenon", International Journal of Cardiology, vol. 65 (Suppl. 1) (1998); pp. S23-S28.

Michishita et al., "A Novel Contrast Removal System from the Coronary Sinus Using an Absorbing Column During Coronary Angiogaphy in a Porcine Model", *Journal of the American College of Cardiology*, vol. 47, No. 9, 2006; 6 pages.

Resnic, F. et al., "No-Reflow is an independent Predictor of Death and Myocardial Infarction after Percutaneous Coronary Intervention", American Heart Journal, vol. 145, No. 1, (2003); pp. 42-46.

Schräder, "Contrast: Media-Induced Renal Failure: An Overview", *Journal of Interventional Cardiology*, vol. 18, No. 6; (2005); pp. 417-423.

del Monte et al., "Improvement in Survival and Cardiac Metabolism After Gene Transfer of Sarcoplasmic Reticulum CA2+-ATPase in a Rat Model of Heart Failure", Circulation, 104(12): 1424-1429, 2001.

Hajjar et al., "Modulation of Ventricular Function Through Gene Transfer in Vivo", Proc. Natl. Acad. Sci., USA, 95: 5251-5256, 1998.

Logeart, D. et al., "How to Optimize In Vivo Gene Transfer to Cardiac Myocytes: Mechanical or Pharmacological Procedures?", Human Gene Therapy, 12: 1601-1610, 2001.

(56) References Cited

OTHER PUBLICATIONS

PCT International Search Report and Written Opinion in Application PCT/US2009/051336, mailed Feb. 19, 2010, 13 pgs.

Fried, Steven et al., "Safe, compact and portable system for regional chemotherapeutic hyperthermic perfusion procedures", Journal of Extra-corporeal Technology, vol. 25, No. 1, pp. 22-26 (1993).

* cited by examiner

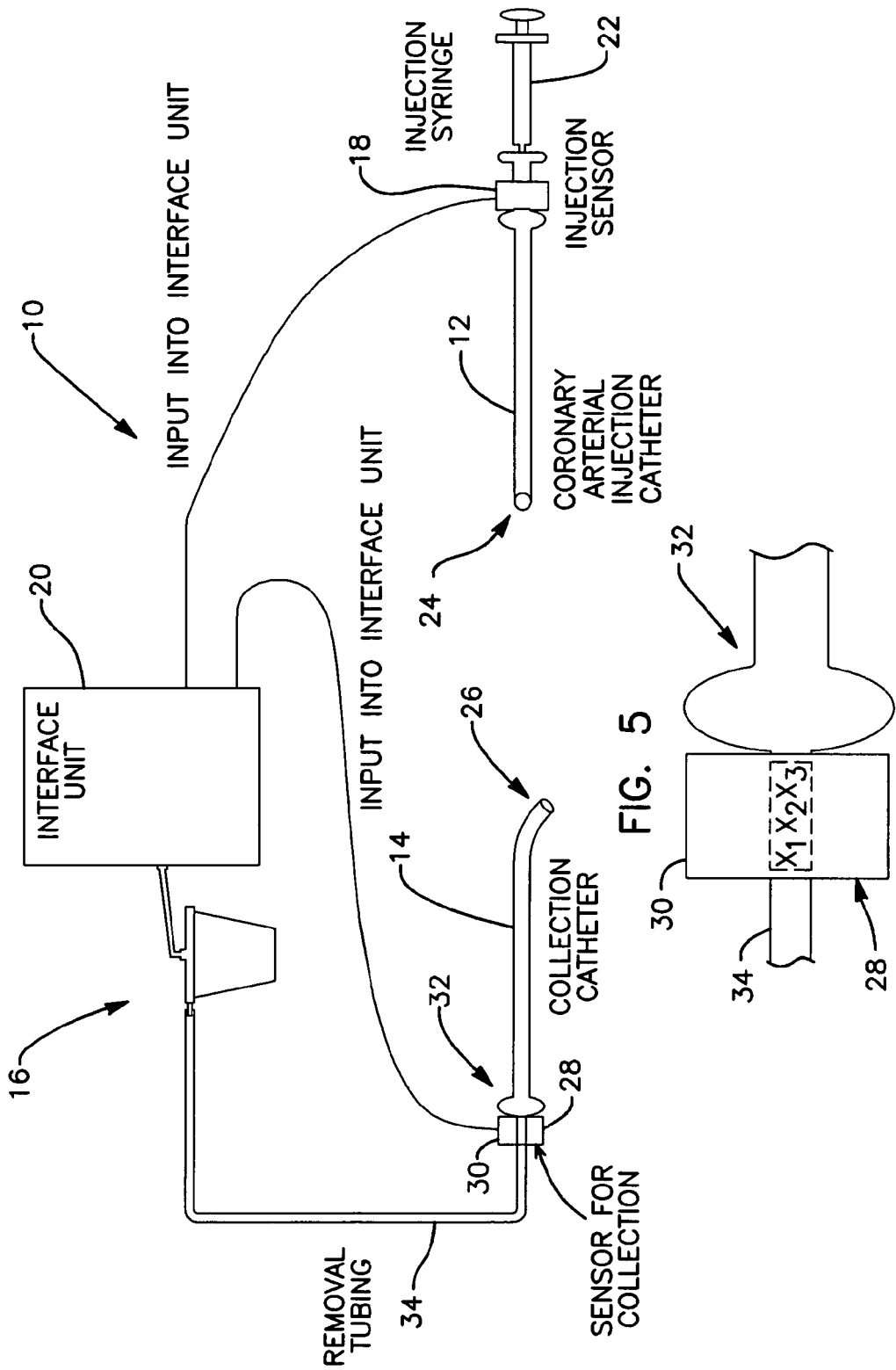

REMOTE SENSING CATHETER SYSTEM AND METHODS

FIELD OF THE TECHNOLOGY

The present disclosure relates generally to devices and systems for use in the medical field, and various methods associated with such devices and systems. More particularly, this disclosure relates to devices and systems used in medical procedures involving the removal of a medium from coronary circulation, and various methods associated therewith.

BACKGROUND

Coronary circulation is the circulation of blood in the vessels that supply blood to and from the heart muscle (the myocardium). The heart is supplied by the right and left coronary arteries and is drained mainly by veins that empty into the coronary sinus.

Angiography is a medical imaging technique in which an X-ray or fluoroscopic image is taken to visualize the lumen of blood vessels and organs of the body. To assist in the visualization process, a contrast media may be added to the blood.

One of the more common angiography procedures performed is the visualization of the coronary arteries. Typically in this procedure, a catheter is used to administer the contrast media into one of the two major coronary arteries. X-ray images of the contrast media within the blood allow visualization of the size, anatomy, and patency of the arterial vessels.

Contrast media, however, can have significant health risks if permitted to flow systemically to the patient's organs. For example, renal dysfunction or failure may occur from such systemic delivery of contrast media. Such dysfunction or failure is referred to as "contrast-induced nephropathy" or CIN.

Systems and methods have been developed for the removal of contrast media and other mediums from the coronary circulation. For example, in some removal methods, a removal catheter is positioned to collect medium as it exits the coronary circulation. In general, conventional systems used to collect and remove medium from the coronary circulation, and the associated conventional methods, can be improved.

SUMMARY

The present disclosure relates to a catheter system used in removing a medium from coronary circulation. In one aspect, the catheter system functions to determine the timing of removal, and is based upon a start time and a volume of an injection. In another aspect, the catheter system employs the use of at least one external sensor.

A variety of examples of desirable product features or methods are set forth in part in the description that follows, and in part will be apparent from the description, or may be learned by practicing various aspects of the disclosure. The aspects of the disclosure may relate to individual features as well as combinations of features, including combinations of features disclosed in separate embodiments. It is to be understood that both the foregoing general description and the following detailed description are explanatory only, and are not restrictive of the claimed invention.

BRIEF DESCRIPTION OF THE DRAWINGS

FIG. 4 is a schematic representation of another embodiment of a sensing catheter system, in accordance with the principles disclosed; and FIG. 5 is an enlarged view of a collection sensor of the sensing catheter system of FIG. 4.

DETAILED DESCRIPTION

Reference will now be made in detail to exemplary aspects of the present disclosure that are illustrated in the accompanying drawings. Wherever possible, the same reference numbers will be used throughout the drawings to refer to the same or like parts.

Contrast media is used to visualize the coronary vasculature as part of coronary diagnostic and therapeutic interventional procedures. The contrast media is toxic to the kidneys and may cause kidney impairment (contrast induced nephropathy), especially in patients with pre-existing kidney disease. Accordingly, contrast removal devices and procedures including catheters for the collection and removal of contrast have been developed. The procedures include inserting the catheter into the coronary sinus (the main vein draining the heart). As the injected contrast media passes through the heart and arrives in the coronary sinus, a negative pressure is applied to the catheter and the contrast mixed with blood is removed from the body. Continuous collection or removal of fluid from the coronary sinus can cause excessive blood loss. Therefore, timing of the removal is critical.

The present system and method relate to the timing of contrast removal from a vessel, such as the coronary sinus. In determining the most effective time for removal of contrast media from the coronary sinus, several events and/or factors are considered.

One factor is the transit time through the myocardium, from coronary artery to coronary sinus. Transit time has been studied in patients with normal and diseased coronary arteries. In the study, a marker solution was injected into the coronary artery; the arrival of the marker as well as the washout of the marker through the coronary sinus was monitored. The results of this study demonstrate that the transit time is relatively consistent for patients with normal coronary arteries. In particular, the marker arrived in the coronary sinus within two seconds after the start of a coronary arterial injection, and washed through the coronary sinus within an average of seven to eight seconds. Patients with obstructed coronary arteries exhibited similar transit time profiles, only with a slightly lengthened washout time. Other published studies as well as direct observations, show the transit time for contrast injected in the coronary arteries to arrive in the coronary sinus is within 4 to seconds. The longer transit time for contrast may be due to its increased viscosity. The present method and system utilizes this information to improve upon conventional methods of removing a medium from the coronary sinus.

Figure 1:
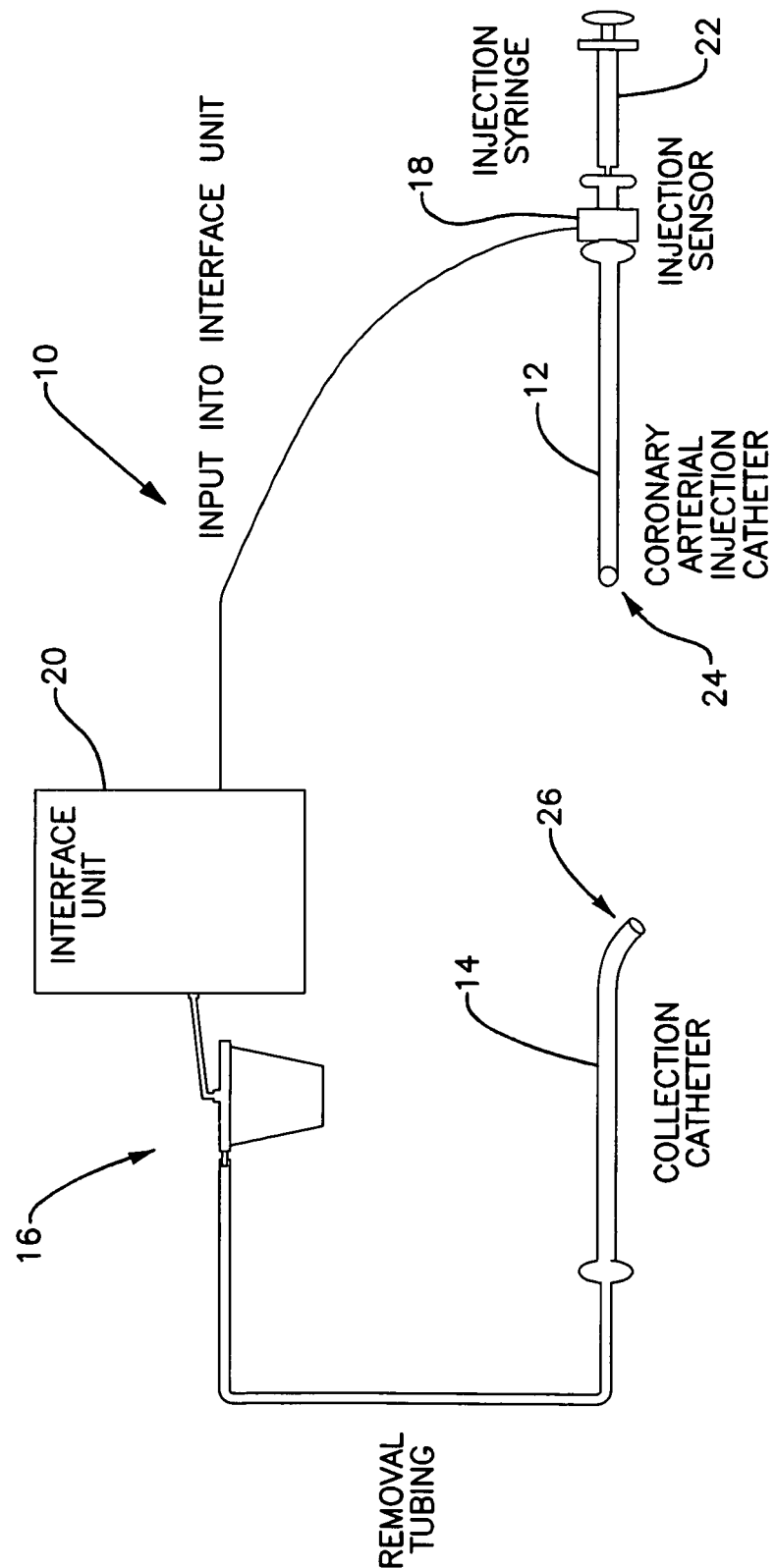
FIG. 1 is a schematic representation of one embodiment of a sensing catheter system, in accordance with the principles disclosed.

Referring now to FIG. 1, a schematic representation of a remote sensing catheter system 10 for removing a medium from a patients' coronary circulation system is illustrated. It is to be understood that "medium" includes, for example, both contrast media and other non-contrast media, such as detection agents (e.g., saline). The system 10 generally includes an injection catheter 12, a collection catheter 14, and a vacuum or aspiration unit 16 that is in fluid communication with the collection catheter 14.

The system 10 further includes an injection sensor 18 and an interface unit 20. The interface unit 20 is electrically connected to both of the injection sensor 18 and the aspiration unit 16. During use, the interface unit 20 controls the operation of the collection catheter 14. What is meant by 'controls the "operation" of collection catheter' is that the interface unit 20 controls the activation and deactivation of the aspiration unit 16, which is in fluid communication with the collection catheter 14.

In some removal devices, a sensor is incorporated into a removal catheter and positioned internal to the coronary circulation system of the patient. The sensor is used to detect the arrival of contrast in a coronary vessel. Such internal sensors add significant complexity and cost into the design and manufacturing of the removal catheter. The present system provides a less complex and less costly design than that of systems having sensors placed within a patient's body during use. In particular, the injection sensor 18 of the present system 10 is remote, or located external to the patients' body during use of the system. In the illustrated embodiment, the injection sensor 18 is located between an injection syringe 22 and the injection catheter 12.

Referring still to FIG. 1, during use of the system 10, a distal end 24 of the injection catheter 12 is positioned within the patient's coronary artery. A distal end 26 of the collection catheter 14 is positioned within the patients' coronary sinus. In one method, the injection sensor 18 is then utilized to activation or start the removal and/or collection of a medium that has been injected into the patient's coronary artery through the injection catheter 12. Preferably, the removal starts at the time when the medium arrives in the coronary sinus to maximize the removal of the medium and minimize the removal of blood.

In particular, in the one method, the syringe 22 is used to inject the medium into the injection catheter 12. The injection of the medium is detected in the injection catheter 12 by way of the injection sensor 18 prior to the medium reaching the patient's coronary artery. The sensor 18 can include a pressure sensor, flow sensor, impedance sensor, or other sensor that detects or measures a specific parameter of an injection, or of the medium in the injection.

Figure 2:
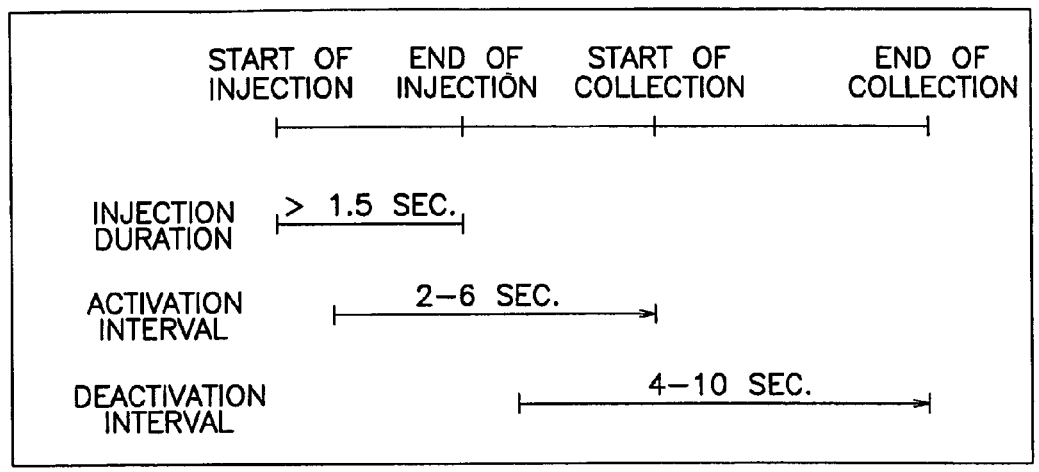
FIG. 2 is a one time line illustrating operation of the sensing catheter system of FIG. 1.
Figure 3:
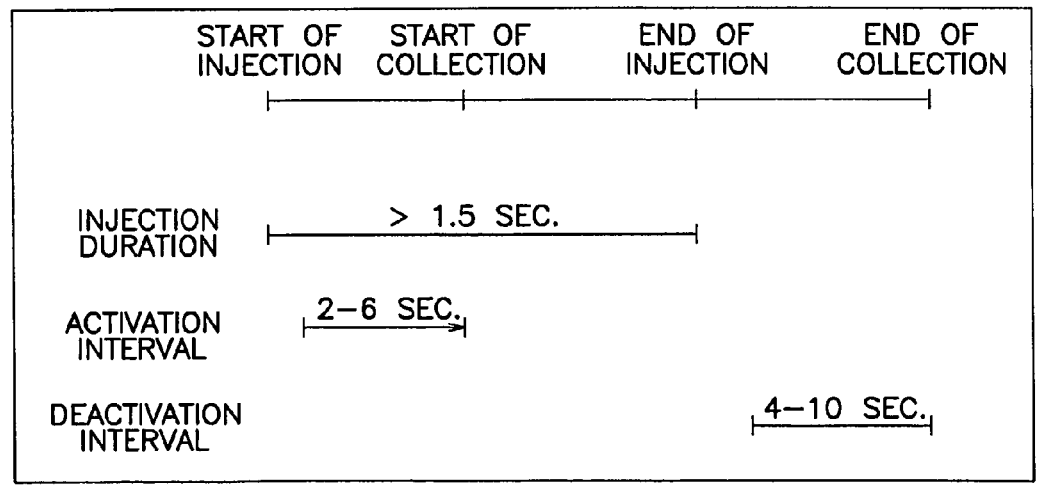
FIG. 3 is a another time line illustrating operation of the sensing catheter system of FIG. 1.

The sensor 18 establishes a start time of the injection. Operation of the collection catheter is then automatically initiated at a predetermined time after the start time of the injection. What is meant by "automatically" is that the operation is initiated by way of the interface unit 20, as opposed to manually initiating operation (i.e., manually activating the aspiration unit 16 and/or interface unit 20). The predetermined time after the start time of the injection typically includes a delay to account for the transit time of the medium so that operation of the collection catheter coincides with the arrival of the medium in the coronary sinus. Referring to FIGS. 2 and 3, in one method, the predetermined time after the start time (labeled Activation Interval) is about 2 to 6 seconds after the start time. In another method, the predetermined time is 4 to 6 seconds after the start time.

In general, the remote sensing catheter system 10 starts or initiates removal of a medium based on the timing from a coronary arterial injection. In addition to determining the timing for removal, the present system 10 can be used to determine whether or not the coronary arterial injection is of a significant amount to warrant activation of the system.

In particular, physicians commonly introduce a small dosage of medium (often referred to as a "puff") into the coronary artery for evaluation purposes. The small puffs are sometimes introduced prior to a significant injection amount, and are sometimes introduced after a significant injection amount to evaluate the ongoing procedure. Collecting fluid from the coronary sinus after the injection of a puff is typically not recommended as more blood than medium is removed, which can lead to excessive blood loss depending upon the number of puffs employed during the procedure.

The present system 10 can be used to determine whether the injection is a puff of medium or a significant amount of medium that warrants removal. In particular, the injection sensor 18 can be used to determine the volume of medium in the injection. In one method, the interface unit 20 initiates operation of the collection catheter 14 only when the volume of medium in the injection is greater than a predetermined amount. Smaller volumes of medium (puffs) are ignored and operation of the collection catheter is not initiated.

In one embodiment, the determination of the volume of medium in the injection is based upon the duration of the injection. If the injection lasts longer than a predetermined duration parameter, then a significant injection amount is declared and operation of the collection catheter is initiated at the predetermined time. Referring to FIGS. 2 and 3, the duration of injection that defines a significant injection amount is defined by an injection duration that is greater than 1.5 seconds. As can be understood, the duration of the injection can end prior to initiating operation of the collection catheter (FIG. 2) or end after initiating operation of the collection catheter (FIG. 3).

The injection sensor 18 of the present system 10 can further be used to determine the timing of ceasing operation of the collection catheter 14. In such a method, the sensor 18 establishes an end time of the injection, as well as the start time. Operation of the collection catheter is then automatically ceased a predetermined time after the end time of the injection. What is meant by "automatically" is that the operation is ceased by way of the interface unit 20, as opposed to manually ceasing operation (i.e., manually deactivating the aspiration unit 16 and/or interface unit 20). Referring to FIGS. 2 and 3, in one method, the predetermined time after the end time (labeled Deactivation Interval) is about 4 to 10 seconds after the end time. Accordingly and in one method, operation of the collection catheter is initiated 2-6 seconds after the start time of the injection and ceases 4 to 10 seconds after the end time of the injection; the duration of operation of the collection catheter typically being between 4 to 6 seconds.

In an alternative embodiment, the timing of ceasing operation of the collection catheter 14 can be determined by use of a sensor. Referring now to FIG. 4, the remote sensing catheter system 10 includes a collection sensor 28 that can be used to cease operation of the collection catheter 14 after a desired majority of the medium has been removed from the coronary circulation. The interface unit 20 is electrically connected to the collection sensor 28 as well as the injection sensor 18 and the aspiration unit 16. The collection sensor 28 is remote, or located external to the patients' body during use of the system 10. The external collection sensor provides a less complex and less costly design than that of systems having internal sensors placed within a patient's body during use. In the illustrated embodiment, the collection sensor 28 is located between the collection catheter 14 and the aspiration unit 16.

The collection sensor 28 detects or senses the presence and/or absence of medium in the collection catheter 14. The sensor 28 can include an impedance sensor. Referring to FIGS. 4 and 5, in one embodiment, the sensor 28 includes an electrode array (e.g., x1, x2, x3) located within a disposal hub assembly 30 connected between a proximal end 32 of the collection catheter 14 and connection tubing 34 of the aspiration unit 16. Optical sensors, chemical sensors, density sensors, or other sensors that detect or measure a specific parameter of an injection or medium in the injection can also be used. In use, when the absence, for example, of the medium in the collection catheter 14 is detected, operation of the collection catheter is automatically ceased.

Still referring to FIG. 4, it is to be understood that alternative systems may include only the external collection sensor 28 (no injection sensor 18). In such a system, the physician would manually actuate operation of the collection catheter 14 a period of time, e.g., 2 to 3 seconds, after starting the injection. Likewise and referring to FIG. 1, in a system including only an external injection sensor, a physician can also manually cease operation of the collection catheter 14 a period of time after the end of the injection.

The above specification provides a complete description of the present invention. Since many embodiments of the invention can be made without departing from the spirit and scope of the invention, certain aspects of the invention reside in the claims hereinafter appended.

What is claimed is:

1. A system that removes a coronary artery injection of medium from a coronary sinus, the system comprising:
    a) a collection catheter having a distal end positionable within a coronary sinus;
    b) an aspiration device in fluid communication with the collection catheter;
    c) an injection device;
    d) an injection catheter having a distal end positionable proximate a coronary artery;
    e) an injection sensor that cooperates with at least one of the injection device and the injection catheter, wherein the injection sensor is located proximate the injection catheter and external to a patient's body during use, and is adapted to detect an injection of a medium in the injection catheter; and
    f) an interface unit, the interface unit being electrically connected to the injection sensor and the aspiration device, wherein the interface unit:
        i) establishes a start time of the coronary artery injection of medium when the injection sensor detects the injection of the medium;
        ii) determines a significance of the volume of medium;
        iii) initiates aspiration by the aspirating unit to the collection catheter about 2 seconds to about 6 seconds after the start time of the injection, the initiation of operation occurring only if, and when, the volume of medium in the injection is determined to be significant; and
        iv) ceases operation of the aspiration unit to the collection catheter after about 4 seconds to about 10 seconds after a cessation of a significant injection.

2. The system of claim 1, wherein the interface unit determines the significance of the volume of medium in the injection based upon a time duration of the injection.

3. The system of claim 2, wherein the interface unit determines the significance of the volume of medium as corresponding to the time duration of the injection being at least one of and greater than 1.5 seconds.

4. The system of claim 1, wherein during use, the injection sensor detects the injection prior to the injection of medium reaching the coronary artery.

5. The system of claim 1, wherein the injection sensor is a pressure sensor.

6. The system of claim 1, wherein the collection sensor is an impedance sensor.

7. The system of claim 1, wherein the injection of medium is an injection of contrast media.

8. The system of claim 1, wherein the injection sensor is part of the injection device.

* * * * *